United States Patent [19]

Blackman

[11] Patent Number: 4,813,538

[45] Date of Patent: Mar. 21, 1989

[54] RE-USABLE STERILE PARENTERAL FLUID MEDICATION ADMINISTRATION KIT

[76] Inventor: Seymour N. Blackman, 1530 Palisade Ave., Fort Lee, N.J. 07024

[21] Appl. No.: 27,937

[22] Filed: Mar. 19, 1987

[51] Int. Cl.[4] .............................................. B65D 81/00
[52] U.S. Cl. .................................. 206/210; 206/205; 206/366
[58] Field of Search ............... 206/210, 205, 364, 365, 206/366

[56] References Cited

U.S. PATENT DOCUMENTS

| 2,346,725 | 4/1944 | Butzke | 206/210 |
| 2,558,742 | 7/1951 | Ericsson et al. | 206/210 |
| 2,666,967 | 1/1954 | Poitras | 206/366 X |
| 2,740,516 | 4/1956 | Renn | 206/365 X |
| 2,755,920 | 7/1956 | Weckman | 206/366 |
| 2,801,738 | 8/1957 | Gabriel | 206/366 X |
| 2,835,377 | 5/1958 | May et al. | 206/366 |
| 3,292,776 | 12/1966 | Penn | 206/366 X |

FOREIGN PATENT DOCUMENTS

| 1067185 | 10/1959 | Fed. Rep. of Germany | 206/365 |
| 3306 | of 1913 | United Kingdom | 206/210 |

Primary Examiner—William Price
Attorney, Agent, or Firm—Kirschstein, Kirschstein, Ottinger & Israel

[57] ABSTRACT

A parenteral fluid medication administration kit includes re-usable barrel, needle and lancet sub-assemblies, each separately mounted in sterilizing positions within a container in which sterilizing fluid is stored. The barrel subassembly may be coupled to, or de-coupled from, either the needle or lancet sub-assemblies. Each use is made under sterile conditions.

16 Claims, 3 Drawing Sheets

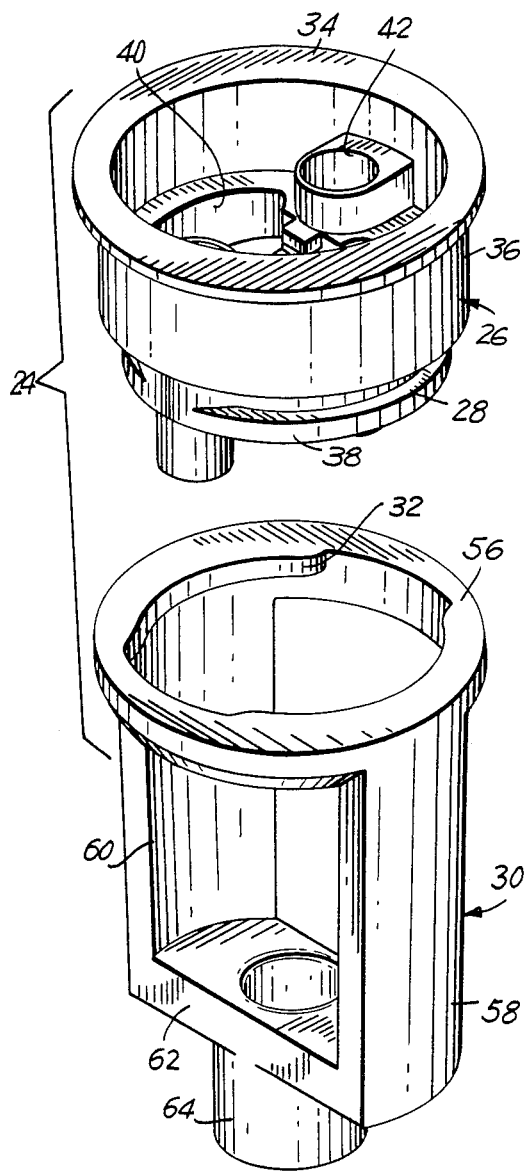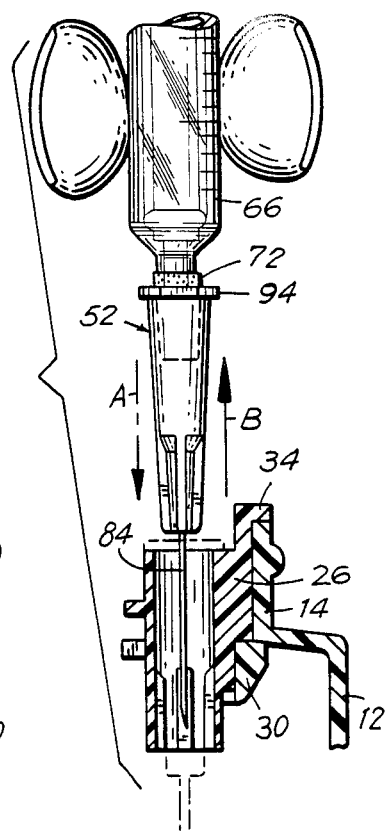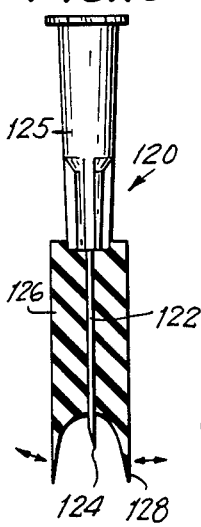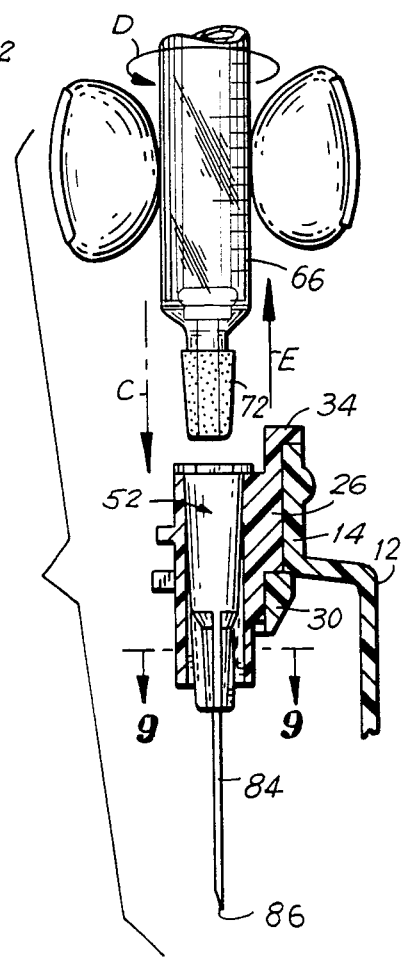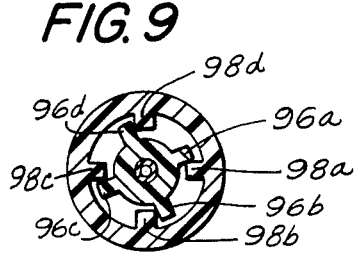

RE-USABLE STERILE PARENTERAL FLUID MEDICATION ADMINISTRATION KIT

BACKGROUND OF THE INVENTION

1. Field of the Invention

This invention generally relates to a parenteral fluid administration kit and method and, more particularly, to parenterally administering fluid medication with re-usable components under sterile conditions for each use.

2. Description of Related Art

For patients requiring the parenteral administration of fluid medication, it is known to utilize throw-away syringes with attached needles which are packed in their own hermetically sealed pouches, manufactured under sterile conditions in order to prevent contamination of the syringes. Once a pouch is opened, it is intended to be used immediately to prevent the syringe, which is now exposed to the germ-laden environment, from becoming contaminated and, hence, unsafe to use.

For patients requiring medication injections on an infrequent basis, it is a minimal expense to discard the syringe after its use. However, for patients, such as diabetics, who require at least one, and sometimes multiple, injections of insulin each day, the expense of throwing away syringes mounts up. Although such patients could sterilize the syringes by boiling them after each use, as some hospitals and medical personnel used to do and still sometimes do, experience has shown that most patients do not have the time or the inclination to bother with such boiling and, as a result, reluctantly incur the ever-mounting costs of discarding such syringes, or bear the risk of exposing themselves to infection by using non-sterilized syringes.

Syringes with attached needles are not the only things which diabetics are intended to routinely discard. Before the injection is given, the diabetic frequently wishes to test his or her own blood glucose level for diagnostic purposes. For that reason, lancets are used to prick and draw blood from the diabetic. An alcohol-saturated pad is used to sterilize not only the pricking site, but also the injection site. The pads and lancets are intended to be discarded after each use, and represent another non-negligible medical treatment cost.

Still another problem in this field regards the relatively large space required for a diabetic to store all of the above paraphernalia. In other words, a plurality of syringes with attached needles, a plurality of lancets, a plurality of pads and an alcohol supply, together with appropriate vials of insulin, occupy a considerable amount of space. When one is at home for each injection, the space requirement is not so critical, but when one works or travels, space is more limited, and it would be more desirable to minimize the space requirement for such paraphernalia when one is away from home.

Recent drug abuse and safety guidelines dictate that any discarded syringes be destroyed, or at least their attached needles be clipped, prior to discarding the syringe. Experience has shown that many individuals, either deliberately or inadvertently, do not observe such guidelines.

SUMMARY OF THE INVENTION

1. Objects of the Invention

It is a general object of this invention to overcome the aforementioned drawbacks in the prior art of administering fluid medication.

It is another object of this invention to parenterally administer fluid medication employing reusable components under sterile conditions for each use.

It is a further object of this invention to separately store and sterilize re-usable syringe components and associated paraphernalia.

Still another object of this invention is to provide a compact, re-usable, sterile parenteral fluid medication kit and method for reliably administering such medication.

Yet another object of this invention is to reduce the expense and minimize the trouble involved in discarding lancets, syringes with attached needles, alcohol-saturated pads and similar paraphernalia.

2. Features of the Invention

In keeping with these objects, and others which will become apparent hereinafter, one feature of this invention resides, briefly stated, in a re-usable, sterile, parenteral fluid medication administration kit which comprises a container, sterilizing fluid in the container, and re-usable syringe means. The syringe means is normally stored in the container in a storage condition. The syringe means is removable from the container to a use condition in which fluid medication is parenterally administered. The syringe means includes a re-usable barrel subassembly and a discrete re-usable needle subassembly.

Optionally, a discrete re-usable lancet subassembly may be stored in the container.

Means are provided for supporting each barrel, needle and lancet subassembly in the container at separate sterilizing positions in which at least a part of each subassembly is immersed in the sterilizing fluid to sterilize at least the immersed parts of each subassembly in the storage condition.

Means are further provided for coupling the barrel subassembly to either the lancet subassembly for pricking purposes, or the needle subassembly for injection purposes, in each use condition. Means are still further provided for de-coupling the barrel subassembly from either the lancet subassembly or the needle subassembly upon return of a respective subassembly to its respective storage condition.

Hence, in accordance with this invention, at least the immersed parts of the subassemblies are sterilized after each pricking or parenteral administration of fluid medication. No longer need syringes with attached needles be thrown away since, simply put, this invention proposes re-using them. No longer need lancets be thrown away after each use because, once again, this invention proposes re-using them. No longer need alcohol-saturated pads be discarded after each use because this invention further proposes, as an option, the use of a single pad which can be stored in the container and saturated with sterilizing fluid from the container when desired. No longer need a separate supply of sterilizing fluid such as alcohol be carried about by the user, since the sterilizing fluid is advantageously accommodated in the same container in which the barrel, lancet and needle subassemblies are stored.

The container itself is formed as a cylinder, and is advantageously no more than 6 inches, and preferably 5 inches, high and about 1¾ inches in diameter so that it can conveniently fit inside one's pocket for transport. No longer need the user be concerned about clipping needles or destroying syringes or boiling syringes and needles after each use.

The novel features which are considered as characteristic of the invention are set forth in particular in the appended claims. The invention itself, however, both as to its construction and its method of operation, together with additional objects and advantages thereof, best will be understood from the following description of specific embodiments when read in connection with the accompanying drawings.

BRIEF DESCRIPTION OF THE DRAWINGS

FIG. 6 is an enlarged perspective exploded view of a support mounted in the kit of FIG. 1;

FIG. 7 is a side view partly in section showing removal of a needle subassembly from the container of FIG. 1;

FIG. 8 is a view analogous to FIG. 7, but showing the return of the needle subassembly to the container of FIG. 1;

FIG. 9 is an enlarged view taken along line 9—9 of FIG. 8; and

FIG. 10 is a side view partly in section of a safety lancet subassembly in accordance with this invention.

DETAILED DESCRIPTION OF THE PREFERRED EMBODIMENTS

Figure 1:
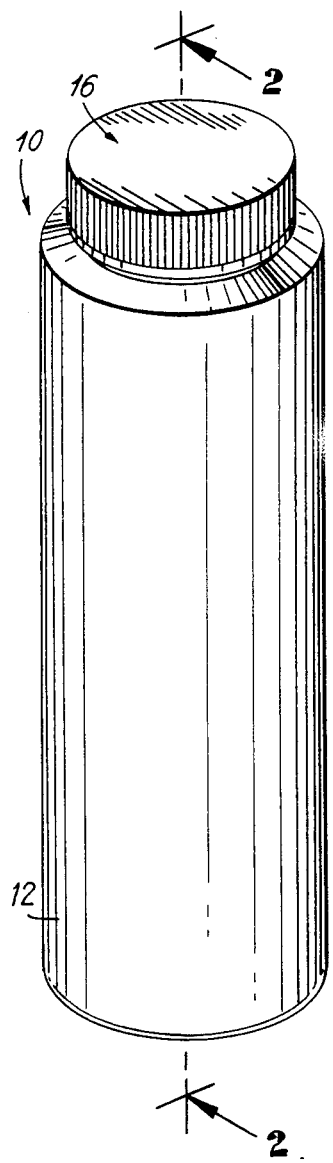
FIG. 1 is a perspective view of a kit in accordance with this invention.
Figure 2:
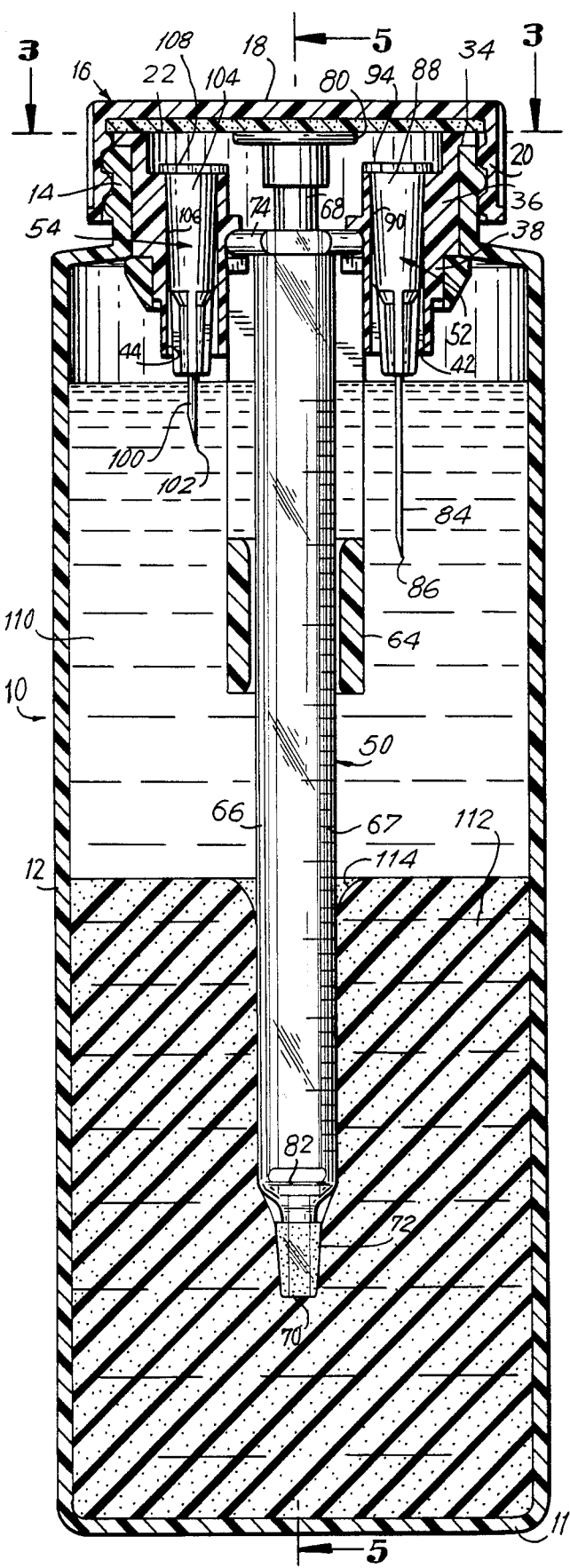
FIG. 2 is an enlarged vertical sectional view taken along line 2—2 of FIG. 1.
Figure 3:
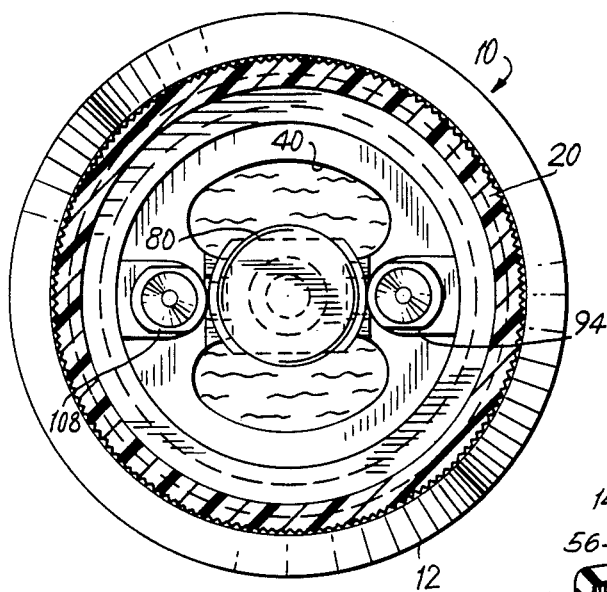
FIG. 3 is a cross-sectional view taken along line 3—3 of FIG. 2.

Referring now to the drawings, reference numeral 10 in FIGS. 1 and 2 generally identifies a re-usable, sterile, parenteral fluid medication administration kit employed for administering such medication in accordance with this invention. Kit 10 includes a cylindrical container 12 having an exteriorly-threaded cylindrical neck 14 centered on, and elongated along, a longitudinal axis. An upper open end of the container is closed by mounting a cap 16 thereon. The cap 16 has a top cap wall 18, and a depending cylindrical skirt 20 which is knurled about an outer peripheral wall to provide a better hand-hold for a user to remove or replace the cap. The skirt 20 is interiorly threaded to mesh with the exteriorly-threaded neck 14. A seal 22 is secured, preferably by adhesive, to the underside of the cap wall 18 and, when the cap is mounted on the container, the seal prevents outward leakage of air and fluid from the container.

A bi-partite plug or support 24, as best shown in FIG. 6, is fitted, and fixedly secured by a frictional tight fit, into the upper open end of the container. The support 24 includes a cup 26 having an exterior thread 28, and a guide 30 having an interior thread 32 which meshes with exterior thread 28 to enable the cup 26 and guide 30 to be detachably interconnected and molded as separate pieces. Cup 26 includes a radially-extending annular rim 34 which engages an outer axial end face of the neck 14, and prevents the cup 26, when fitted onto the container, from falling therein. Cup 26 also includes a first cylindrical section 36 of a predetermined larger diameter which extends axially along the neck, as well as a second cylindrical section 38 of a smaller diameter which extends axially below the neck 14 and into the interior of the container toward a bottom wall 11 thereof.

First wall means bounding an opening 40 is formed through a central region of the support 24 and serves, as described below, for receiving a barrel subassembly 50. Second wall means bounding an opening 42 is formed through one lateral region of the support 24 and serves, as described below, for receiving a needle subassembly 52. Third wall means bounding an opening 44 is formed through an opposite lateral region of the support and serves, as described below, for receiving a lancet subassembly 54.

Figure 4:
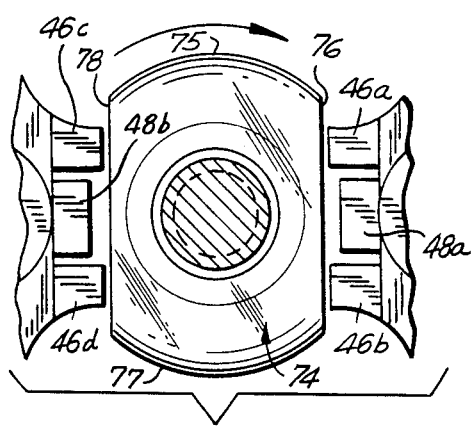
FIG. 4 is a broken-away top plan view depicting a barrel subassembly of the syringe of FIG. 1 being locked in place.

Cup 26 is also provided with mutually-opposing pairs of abutments 46a, 46b, 46c, 46d (see FIG. 4). Abutments 46a, 46b extend into the barrel opening 40 toward, but terminate by a spacing short of, abutments 46c, 46d. All of the abutments have upper surfaces which are at the same predetermined elevation. A pair of opposing hold-down fingers 48a, 48b also extend into the barrel opening 40 toward, but terminate short of, each other. The lower surfaces of the fingers 48a, 48b are located at a higher elevation than said predetermined elevation. Finger 48a is located between abutments 46a, 46b. Finger 48b is located between abutments 46c, 46d. All of the abutments and the fingers extend into the barrel opening 40 in mutual parallelism.

The guide 30 includes a ring 56 from which a pair of depending arms 58, 60 extend axially downwardly away from the ring 56 at opposite sides thereof. A transverse web 62 interconnects lower ends of the arms 58, 60, and lies in a plane generally parallel to the ring 56. A hollow cylindrical guide sleeve 64 extends axially away from the web 62, and bounds a guide passage which is concentric with the ring 56, as well as the barrel opening 40 when the cup 26 is threaded onto the guide 30.

The barrel subassembly 50 includes an elongated transparent barrel 66 having gradations or markings 67 thereon lengthwise of the barrel, thereby indicating the dose of the fluid medication to be parenterally administered. The barrel 66 has an upper end through which a piston 68 extends, and an opposite discharge end 70. A tapered frusto-conical projection 72, also known as a Luer tip, extends from the barrel 66 to the discharge end 70, and is provided about its exterior peripheral wall with a roughened, coarse surface. A flange 74, which may either be circular or, as shown in FIG. 4 in a preferred embodiment, may be non-circular with a pair of opposed flats 76, 78, is provided at the upper barrel end. The flats 76, 78 are spaced apart by a predetermined distance which is less than the aforementioned spacing between the pairs of abutments. The flange 74 also has curved edges 75, 77 which are spaced apart at their maximum extent by a distance greater than said predetermined spacing between the pairs of abutments.

The barrel subassembly 50 also includes an outer handle 80 provided at one end of the piston 68 and, at its opposite end, an O-ring seal 82. The piston 68 is mounted in, for sliding movement along, the barrel 66.

The needle subassembly 52 includes an injection needle 84 having a sharp pointed tip 86, and a needle holder 88 in which a tapered frusto-conical seat 90 is formed. An annular lip 94 is formed at the end of the holder 88 opposite the needle 84. As best shown in FIG. 9, a set of axially-extending ribs 96a, 96b, 96c, 96d are equi-angularly arranged, and extend along, the exterior of the holder 88. A corresponding plurality of splines 98a, 98b, 98c, 98d are equi-angularly arranged around, and extend axially along, the interior of the needle passage 42. The splines and ribs together serve, as described below, as anti-turning locking means operative for de-coupling the needle and barrel subassemblies.

The lancet subassembly 54 includes a pricking lance 100 having a sharp pointed pricking tip 102, and a lancet holder 104 in which a tapered frusto-conical seat 106 is formed. An annular lip 108 is formed at the end of the holder 104 opposite the lance 100. Analogous to that described earlier, a set of axially-extending ribs are equi-angularly arranged around, and extend along, the exterior of holder 104. A corresponding plurality of splines are equi-angularly arranged around, and extend axially along, the interior of lancet opening 44. These splines and ribs are operative, as described below, for de-coupling the lancet and barrel subassemblies.

The container 12, advantageously formed of thin plastic material, is filled with a sterilizing fluid 110, preferably alcohol, operative for sterilizing those parts of the subassemblies 50, 52, 54 immersed therein. As shown in FIG. 2, after the barrel, needle and lancet subassemblies 50, 52, 54 are respectively supportably received in openings 40, 42, 44 and suspended from the support 24 for immersion of their lower ends into the alcohol, the alcohol sterilizes the immersed parts. Thus, the injection needle 84 and the lance 100 are sterilized over their entire lengths, or substantially so. Also, virtually the entire barrel 66 is sterilized, not only over its exterior, but also its interior surface, since the alcohol is free to enter the discharge end 70 into the barrel 66.

Biasing means, advantageously constituted by a resilient sponge 112, is fittingly secured in the lower end region of the container 12 adjacent the bottom wall 11, and is likewise immersed in the alcohol which enters in the interstices thereof. The sponge 112 is advantageously pre-formed with a central opening 114, or is slit to form an opening, into which the leading end of the barrel 66 is longitudinally inserted into pressing engagement with the sponge. The pressed sponge, seeking to return to its initial undeformed state, constantly biases the barrel subassembly 50 upwardly. With the cap 16 mounted on the container, the biasing action merely serves to affirmatively urge the handle 80 of the piston 68 into tighter engagement with the cap wall 18. However, once the cap is removed, the biasing action serves to automatically lift the barrel subassembly 50 into the waiting hands of a user, thereby enabling the user to gain more ready access to the barrel subassembly so that the latter can be easily removed from the container. During such lifting movement, the barrel 66 is guided along the longitudinal direction by the guide sleeve 64 which prevents lateral shifting of the barrel 66.

The kit thus comprises the barrel, needle and lancet subassemblies 50, 52, 54, each separately longitudinally inserted and supported in respective openings 40, 42, 44 which are all located at different, separate, discrete sterilizing positions inside the container. Lips 94 and 108 rest on and support their respective needle and lancet subassemblies on the first cylindrical section 36 of the support, and prevent the needle and lancet subassemblies from falling therethrough and into the alcohol 110. The holders 88, 104 frictionally engage the needle and lancet openings 90, 106. The ribs at the exterior of the holders 88, 104 are situated between adjacent splines within the needle and lancet openings. Flange 74 on the barrel 66 rests on, and is supported by, the upper surfaces of the abutments. If it is desired to lock the barrel subassembly in its barrel opening 40, then the flange 74 is inserted so that the flats 76, 78, as best shown in FIG. 4, clear the aforementioned spacing between the pairs of abutments without mechanical interference. Thereupon, the flange 74 may be turned, for example, through an angular distance of 90°, so that the curved edges 75, 77 are situated above the pairs of abutments but below the hold-down fingers 48a, 48b, thereby capturing the flange 74 therebetween.

Figure 5:
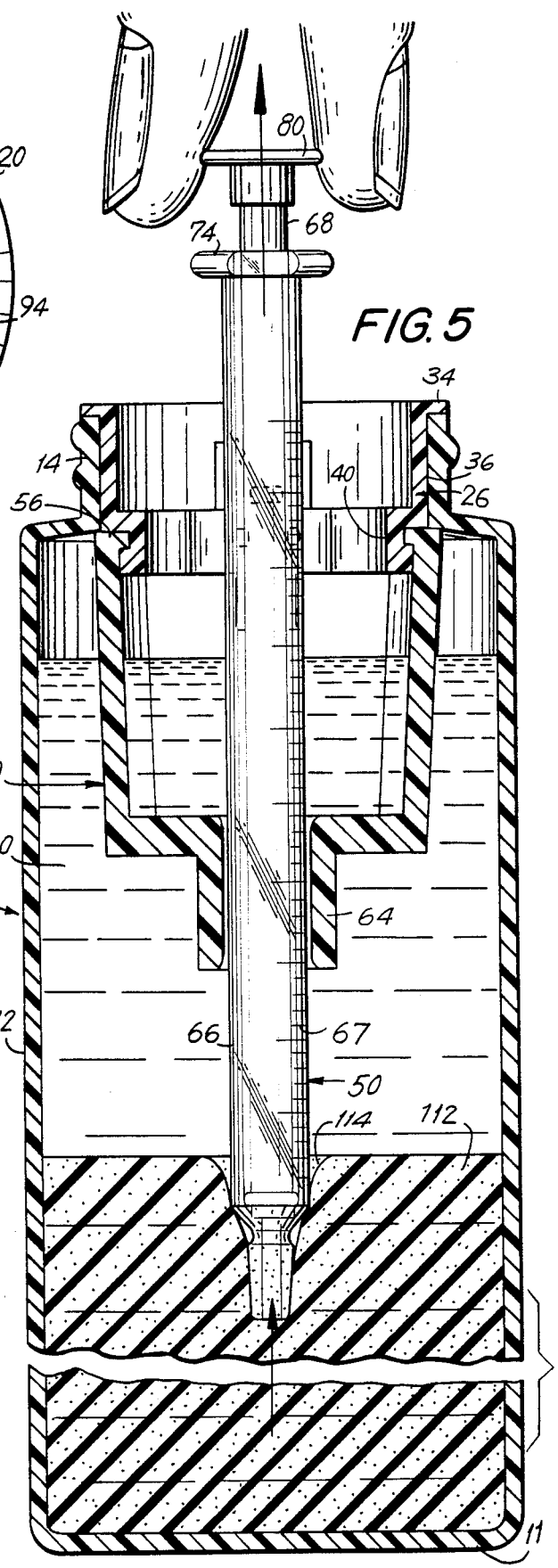
FIG. 5 is a vertical sectional view taken along line 5—5 of FIG. 2.

In use, the user removes the cap 16 from the container. If the flange 74 is captured between the hold-down fingers and the abutments, then it is necessary for the user to turn the barrel subassembly 50 through the angular distance of 90° so that the flats 76, 78 will once again clear the abutments before the barrel subassembly can be lifted out of the container with the aid of the sponge 112 which at least initiates such lifting movement. If the flange is not so captured, then the sponge 112 will automatically lift the barrel subassembly upwardly, as shown in FIG. 5, whereupon the user has ready access to the barrel subassembly above the neck.

With the sterilized barrel subassembly in hand, the user forcefully urges the tapered projection 72 axially into the tapered seat 106 of the lancet subassembly 54 in the direction of arrow A in FIG. 7. Although FIG. 7, and later FIG. 8, show the removal and return of the needle subassembly 52, it will be understood that the same removal and return considerations apply to the lancet subassembly. The projection 72 is thereby wedged into tight frictional engagement with the tapered seat of the lancet holder. This snug fit is augmented by the roughened surface on the projection 72 which bitingly engages the relatively smoother interior surface bounding the seat 106.

The user then removes the barrel subassembly, with the lancet subassembly attached thereon, in the direction of arrow B in FIG. 7. The sterilized lance 100 is now available to be forcefully urged into a pricking site on the user's body in order to draw blood therefrom for diagnostic purposes. It is recommended that the pricking site be initially washed with an alcohol-saturated pad in order to sterilize the pricking site.

Once the blood has been tested, the lancet subassembly 54 is returned to its original storage position within the container and, for that purpose, the lancet subassembly is re-inserted into lancet opening 44 in the direction of arrow C in FIG. 8. Thereupon, the barrel subassembly, which is still attached to the lancet subassembly 54, is turned in the circumferential direction of arrow D in FIG. 8 until the splines located within the lancet opening mechanically interfere with the ribs on the lancet subassembly, eventually releasing the friction fit between the barrel and lancet subassemblies. The released barrel subassembly can now be lifted away from the lancet subassembly in the direction of arrow E in FIG. 8.

Once the lancet subassembly 54 has been returned to its sterilizing position, the barrel subassembly, in a completely analogous manner, can have its tapered projection 72 inserted, this time into the tapered seat of the needle subassembly 52 until a wedged, tight, frictional engagement is made therewith. The user may then remove the barrel subassembly with the needle subassembly attached, and inject himself or herself, or someone else, with fluid medication previously admitted into the barrel 66.

Prior to such injection, it is recommended that the coupled barrel and needle subassemblies, which now constitute a complete syringe, be air-purged by moving the piston 68 up and down the barrel a few times. Thereupon, any residual alcohol in the barrel and in the needle 84 should be shaken from the syringe by holding the flange 74 between the thumb and forefinger and shaking the syringe in a manner similar to shaking the mercury down in a thermometer.

Thereupon, the piston 68 is raised to the appropriate dose line 67. A vial of fluid medication, e.g. insulin, covered with a diaphragm, is preferably swabbed with an alcohol-saturated pad. The needle 84 is then inserted through the diaphragm, and the piston is depressed to the bottom of the barrel. With the vial elevated above the syringe, the piston is once again moved up and down several times to remove air bubbles. Thereupon, the piston is pulled back until the leading edge of the O-ring 82 registers with the proper dose line 67. The loaded syringe is now withdrawn from the vial, the site of injection is swabbed with another or the same alcohol-saturated pad, and the user may now proceed with the injection.

After the injection, the needle subassembly is returned to its initial sterilizing position in a manner analogous to that described above for the lancet subassembly, as shown in FIG. 8. To repeat, the barrel subassembly is turned slightly in the direction of arrow D; the tight fit is eventually broken due to mechanical interference between the ribs on the needle holder and the splines in the needle opening; and then the barrel subassembly is removed in the direction of arrow E, this time without the needle subassembly being attached. The barrel subassembly can now be returned to its initial sterilizing position.

Prior to return of the barrel and needle subassemblies to their respective storage positions within the container, it is recommended that, after each use, the needle 84 is placed under running tap water and, at the same time, the piston is moved several times through the barrel so as to purge the barrel of air. Alcohol may be drawn into the barrel up to, for example, the 10-unit mark, i.e. close to the discharge end 70 of the barrel, and thereupon expelled, thereby sterilizing the lower end of the barrel prior to returning the barrel and needle subassemblies to the container.

The lancet, needle and barrel subassemblies can be re-used, and need not be discarded as in the prior art. These subassemblies conveniently fit within a cylindrical container no more than 6 inches high, and together form a compact storage unit which also advantageously houses the sterilizing fluid. A plurality of lancets, needles and syringes need no longer be stored, discarded or boiled. If desired, the aforementioned alcohol-saturated pad could be stored above the cup 26 and below the cap wall 18 inside the neck 14 of the container, although this has not been shown in the drawings in order not to obscure the same. The pad could be re-used so long as it is sterilized by washing the same with the alcohol after each use.

Another advantageous feature of this invention resides in providing a separate envelope. If the user does not wish to carry the kit on his or her person, then the syringe with the attached needle subassembly can be inserted into the envelope which is thereupon closed to prevent contamination. The envelope can be opened when needed.

Still another feature of this invention resides in providing a modified safety lancet subassembly. As shown in FIG. 10, the lancet subassembly 120 includes a lance 122 having a pointed tip 124, and a lancet holder 125 for holding the lance 122. A resilient sleeve, preferably a rubber grommet 126, is mounted on the holder 124 and closely surrounds the lance 122 along its entire length, except for the tip 124. A conical outwardly-flared lip 128 surrounds the tip 124.

In use, the user presses the lancet subassembly 120 quickly against the pricking site, during which time the lip 128 flexes and deforms out of the way to permit the tip 124 to penetrate the skin. Residence time of the tip 124 in the skin is minimized due to the fact that the deformed lip constantly urges the tip 124 away from the skin due to the inherent resilience of the lip which is seeking to return to its original undeformed state. Thus, the lip 128 moves out of the way during insertion and biases the tip 124 away from the pricking site, thereby insuring that the tip 124 is not located within one's skin for longer than is absolutely necessary to draw blood. Also, the fact that the lip 128 hides the tip 124 from view renders the safety lancet subassembly 120 less objectionable, particularly to squeamish users.

It will be understood that each of the elements described above, or two or more together, also may find a useful application in other types of constructions differing from the types described above.

While the invention has been illustrated and described as embodied in a re-usable sterile parenteral fluid medication administration kit and method, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims:

1. A re-usable, sterile, parenteral fluid medication administration kit, comprising:
    (a) a container;
    (b) sterilizing fluid in the container;
    (c) re-usable syringe means normally stored in the container in a storage condition, and removable from the container to a use condition in which fluid medication is parenterally administered, said syringe means including a re-usable barrel subassembly and a discrete re-usable needle subassembly;
    (d) means for supporting each subassembly in the container at separate sterilizing positions in which at least a part of each subassembly is immersed in the sterilizing fluid to sterilize at least the immersed parts of each subassembly in the storage condition;
    (e) means for coupling the subassemblies in each use condition;
    (f) means for de-coupling the subassemblies upon return of the subassemblies to the storage condition, thereby sterilizing at least the immersed parts of the subassemblies after each parenteral administration of fluid medication; and
    (g) a discrete re-usable lancet subassembly, said supporting means also supporting the lancet subassembly at another separate sterilizing position in which at least a part of the lancet subassembly is immersed in the sterilizing fluid, said coupling means also coupling the barrel and lancet subassemblies in a pricking condition, and said de-coupling means also de-coupling the barrel and lancet subassemblies upon return to the container after the pricking condition has been completed.

2. A re-usable, sterile, parenteral fluid medication administration kit, comprising:
(a) a container having an annular neck centered on a longitudinal axis;
(b) sterilizing fluid in the container;
(c) re-usable syringe means normally stored in the container in a storage condition, and removable from the container to a use condition in which fluid medication is parenterally administered, said syringe means including a re-usable barrel subassembly and a discrete re-usable needle subassembly, said barrel subassembly including an elongated barrel having a discharge end and a flange at an end opposite the discharge end, and a piston mounted in, and movable along, the barrel, and said needle subassembly including an elongated needle having a pointed tip, and a tubular needle holder having an open end;
(d) means for supporting each subassembly in the container at separate sterilizing positions in which at least a part of each subassembly is immersed in the sterilizing fluid to sterilize at least the immersed parts of each subassembly in the storage condition, said supporting means including a support secured to the neck and having first walls bounding a longitudinally-extending barrel passage in which the barrel subassembly is removably mounted, and second walls bounding a longitudinally-extending needle passage in which the needle subassembly is removably mounted, said support including an abutment for supportably engaging the flange in the storage condition, and a collar spaced longitudinally from the abutment and closely surrounding the barrel to prevent transverse shifting of the barrel in the storage condition;
(e) means for coupling the subassemblies in each use condition; and
(f) means for de-coupling the subassemblies upon return of the subassemblies to the storage condition, thereby sterilizing at least the immersed parts of the subassemblies after each parenteral administration of fluid medication.

3. A re-usable, sterile, parenteral fluid medication administration kit, comprising:
(a) a container having an annular neck centered on a longitudinal axis;
(b) sterilizing fluid in the container;
(c) re-usable syringe means normally stored in the container in a storage condition, and removable from the container to a use condition in which fluid medication is parenterally administered, said syringe means including a re-usable barrel subassembly and a discrete re-usable needle subassembly, said barrel subassembly including an elongated barrel having a discharge end, and a piston mounted in, and movable along, the barrel, and said needle subassembly including an elongated needle having a pointed tip, and a tubular needle holder having an open end;
(d) means for supporting each subassembly in the container at separate sterilizing positions in which at least a part of each subassembly is immersed in the sterilizing fluid to sterilize at least the immersed parts of each subassembly in the storage condition, said supporting means including a support secured to the neck and having first walls bounding a longitudinally-extending barrel passage in which the barrel subassembly is removably mounted, and second walls bounding a longitudinally-extending needle passage in which the needle subassembly is removably mounted;
(e) means for coupling the subassemblies in each use condition, said coupling means including a tapered projection at the discharge end of the barrel, and a tapered seat within the needle holder and in communication with the open end, said tapered seat snugly engaging with a predetermined force the tapered projection with a friction-tight fit upon longitudinal insertion of the tapered projection into the tapered seat; and
(f) means for de-coupling the subassemblies upon return of the subassemblies to the storage condition, thereby sterilizing at least the immersed parts of the subassemblies after each parenteral administration of fluid medication, said de-coupling means including anti-turning locking means on the needle holder and in the needle passage for lockingly engaging the second walls bounding the needle passage upon turning the needle holder about an axis parallel to the longitudinal axis with a force greater than said predetermined force, thereby uncoupling the subassemblies.

4. A re-usable, sterile, parenteral fluid medication administration kit, comprising:
(a) a container having an annular neck centered on a longitudinal axis;
(b) sterilizing fluid in the container;
(c) re-usable syringe means normally stored in the container in a storage condition, and removable from the container to a use condition in which fluid medication is parenterally administered, said syringe means including a re-usable barrel subassembly and a discrete re-usable needle subassembly, said barrel subassembly including an elongated barrel having a discharge end, and a piston mounted in, and movable along, the barrel, and said needle subassembly including an elongated needle having a pointed tip, and a tubular needle holder having an open end;
(d) means for supporting each subassembly in the container at separate sterilizing positions in which at least a part of each subassembly is immersed in the sterilizing fluid to sterilize at least the immersed parts of each subassembly in the storage condition, said supporting means including a support secured to the neck and having first walls bounding a longitudinally-extending barrel passage in which the barrel subassembly is removably mounted, and second walls bounding a longitudinally-extending needle passage in which the needle subassembly is removably mounted;
(e) means for coupling the subassemblies in each use condition, said coupling means including a tapered projection having a roughened exterior peripheral wall at the discharge end of the barrel, and a tapered seat within the needle holder and in communication with the open end, said tapered seat having a smooth interior circumferential wall snugly engaging with a predetermined force the tapered projection with a friction-tight fit upon longitudinal insertion of the tapered projection into the tapered seat; and (f) means for de-coupling the subassemblies upon return of the subassemblies to the storage condition, thereby sterilizing at least the immersed parts of the subassemblies after each parenteral administration of fluid medication.

5. The re-usable kit as recited in claim 1, wherein the container has an annular neck centered on a longitudinal axis, and wherein the supporting means includes a support secured to the neck and having first walls bounding a longitudinally-extending barrel passage in which the barrel subassembly is removably mounted, and second walls bounding a longitudinally-extending needle passage in which the needle subassembly is removably mounted.

6. The re-usable kit as recited in claim 5, wherein the barrel subassembly includes an elongated barrel having a discharge end, and a piston mounted in, and movable along, the barrel; and wherein the needle subassembly includes an elongated needle having a pointed tip, and a tubular needle holder having an open end.

7. The re-usable kit as recited in claim 6, wherein the coupling means includes a tapered projection at the discharge end of the barrel, and a tapered seat within the needle holder and in communication with the open end, said tapered seat snugly engaging with a predetermined force the tapered projection with a friction-tight fit upon longitudinal insertion of the tapered projection into the tapered seat.

8. The re-usable kit as recited in claim 6, wherein the needle holder has a lip at the open end of the needle holder, and wherein the support has a base wall for supportably engaging the lip in the storage condition.

9. The re-usable kit as recited in claim 2, wherein the container includes a cap removably mounted on the neck, said cap having a cap wall in overlying engagement with the piston when the cap is mounted on the neck; and further comprising means in the container for urging the barrel subassembly from the storage toward the use condition when the cap is removed from the neck.

10. The re-usable kit as recited in claim 9, wherein the urging means is a resilient member immersed in the sterilizing fluid and bearing against the discharge end of the barrel in the storage condition.

11. The re-usable kit as recited in claim 2, wherein the flange has a non-circular configuration with one predetermined dimension in one radial direction and another dimension smaller than said predetermined dimension in another radial direction angularly spaced from said one radial direction, and wherein the support includes hold-down fingers on opposite sides of the longitudinal axis and spaced radially away from each other by a distance larger than said smaller predetermined dimension to permit the flange to pass by with clearance, but smaller than said larger predetermined dimension to permit the hold-down fingers to capture the flange when the flange is turned angularly.

12. The re-usable kit as recited in claim 4; and further comprising a discrete re-usable lancet subassembly, and wherein the supporting means also supports the lancet subassembly at another separate sterilizing position in which at least a part of the lancet subassembly is immersed in the sterilizing fluid, and wherein the coupling means also couples the barrel and lancet subassemblies in a pricking condition, and wherein the de-coupling means also de-couples the barrel and lancet subassemblies upon return to the container after the pricking condition has been completed.

13. The re-usable kit as recited in claim 1, wherein the lancet subassembly includes a lancet holder and a pricking lance, and wherein the coupling means includes a tapered projection on the barrel subassembly, and a tapered seat within the lancet holder and snugly engaging the tapered projection with a friction-tight fit upon longitudinal insertion of the tapered projection into the tapered seat.

14. The re-usable kit as recited in claim 13; and further comprising safety means on the lancet subassembly for biasing the pricking lance away from a patient during pricking.

15. The re-usable kit as recited in claim 14, wherein the safety means includes a resilient sleeve through which the pricking lance extends, said sleeve having a deformable, outwardly-flared lip which is resiliently deformed during pricking and which jointly urges, due to its inherent resilience, the deformed lip and the pricking lance away from the patient.

16. The re-usable kit as recited in claim 1, wherein the sterilizing fluid is alcohol.

* * * * *